United States Patent
McClintock et al.

(10) Patent No.: US 9,168,068 B2
(45) Date of Patent: Oct. 27, 2015

(54) SPINAL STABILIZATION SYSTEM

(71) Applicant: K2M, Inc., Leesburg, VA (US)

(72) Inventors: Larry McClintock, Gore, VA (US); Brandon Moore, Summit Point, WV (US)

(73) Assignee: K2M, INC., Leesburg, VA (US)

( * ) Notice: Subject to any disclaimer, the term of this patent is extended or adjusted under 35 U.S.C. 154(b) by 228 days.

(21) Appl. No.: 13/675,159

(22) Filed: Nov. 13, 2012

(65) Prior Publication Data
US 2014/0135840 A1    May 15, 2014

(51) Int. Cl.
*A61B 17/70* (2006.01)

(52) U.S. Cl.
CPC ......... *A61B 17/7011* (2013.01); *A61B 17/7032* (2013.01); *A61B 17/7059* (2013.01)

(58) Field of Classification Search
CPC ........... A61B 17/7011; A61B 17/7032; A61B 17/7059
USPC .......... 606/246, 264–270, 279, 301, 305, 308
See application file for complete search history.

(56) References Cited

U.S. PATENT DOCUMENTS

| | | | |
|---|---|---|---|
| 3,997,138 A * | 12/1976 | Crock et al. | 248/67.5 |
| 5,217,497 A | 6/1993 | Mehdian | |
| 5,261,912 A | 11/1993 | Frigg | |
| 5,658,286 A | 8/1997 | Sava | |
| 5,667,508 A | 9/1997 | Errico et al. | |
| 5,800,435 A | 9/1998 | Errico et al. | |
| 5,899,904 A | 5/1999 | Errico et al. | |
| 5,910,142 A | 6/1999 | Tatar | |
| 5,947,969 A | 9/1999 | Errico et al. | |
| 6,102,912 A | 8/2000 | Cazin et al. | |
| 6,451,021 B1 | 9/2002 | Ralph et al. | |
| 6,482,207 B1 | 11/2002 | Errico | |
| 6,540,749 B2 | 4/2003 | Schafer et al. | |
| 6,582,434 B2 | 6/2003 | Kawakami et al. | |
| 6,644,087 B1 | 11/2003 | Ralph et al. | |
| 7,503,918 B2 | 3/2009 | Baccelli et al. | |
| 7,520,879 B2 | 4/2009 | Justis et al. | |
| 7,563,274 B2 | 7/2009 | Justis et al. | |
| 7,569,061 B2 | 8/2009 | Colleran | |
| 7,588,575 B2 | 9/2009 | Colleran et al. | |
| 7,588,588 B2 | 9/2009 | Spitler et al. | |
| 7,604,653 B2 | 10/2009 | Kitchen | |
| 7,618,442 B2 | 11/2009 | Spitler et al. | |
| 7,766,942 B2 | 8/2010 | Patterson et al. | |

(Continued)

*Primary Examiner* — Pedro Philogene
*Assistant Examiner* — David Comstock
(74) *Attorney, Agent, or Firm* — Carter, DeLuca, Farrell & Schmidt, LLP

(57) ABSTRACT

A spinal stabilization system includes an elongated loop member and a bone screw. The elongated loop member includes a pair of opposing elongate bodies defining a gap therebetween and a pair of connection members connecting the pair of opposing elongate bodies at opposite ends of the elongate bodies. The bone screw includes a head portion defining a slot, a shank extending longitudinally from the head portion and a set screw. The slot includes a leading end portion configured to receive at least a portion of the elongated loop member and a trailing end portion adapted to receive the set screw. The gap defined by the pair of opposing elongate bodies is dimensioned to receive at least a portion of the bone screw securely connected to one of the pair of opposing elongate bodies. The gap is configured and dimensioned to facilitate unilateral adjustment of the elongated loop member relative to the bone screw.

14 Claims, 6 Drawing Sheets

(56) References Cited

U.S. PATENT DOCUMENTS

| | | |
|---|---|---|
| 7,931,676 B2 | 4/2011 | Veldman et al. |
| 8,226,695 B2 | 7/2012 | Moore et al. |
| 2002/0161368 A1 | 10/2002 | Foley et al. |
| 2005/0065515 A1 | 3/2005 | Jahng |
| 2007/0093817 A1 | 4/2007 | Barrus et al. |
| 2008/0027432 A1 | 1/2008 | Strauss et al. |
| 2008/0086130 A1 * | 4/2008 | Lake et al. .............. 606/61 |
| 2010/0094357 A1 | 4/2010 | Wallenstein et al. |

* cited by examiner

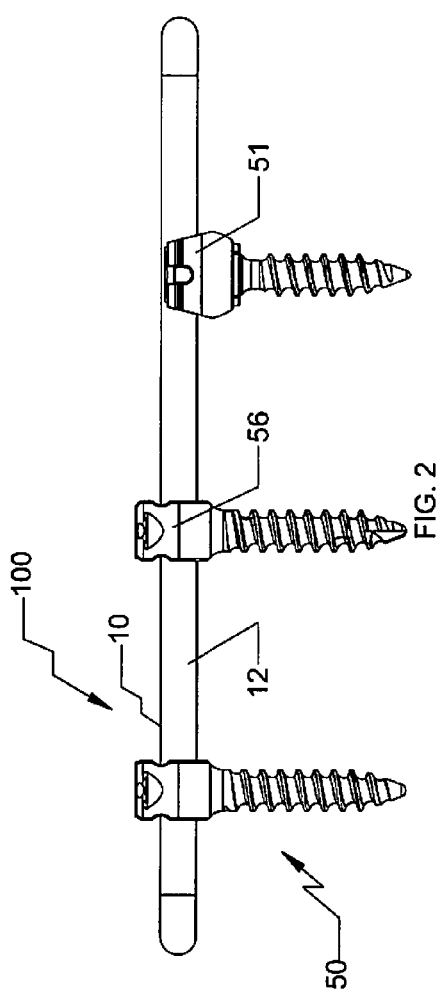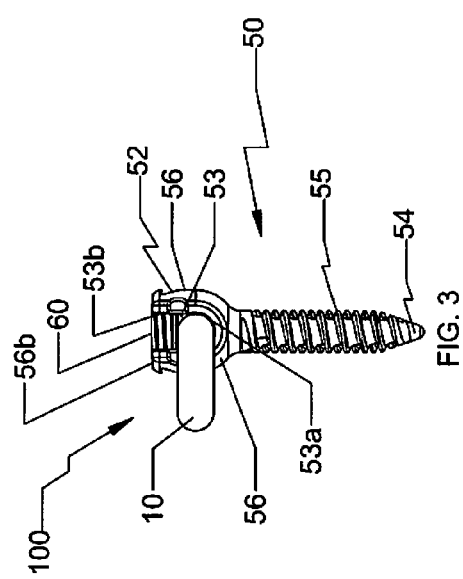

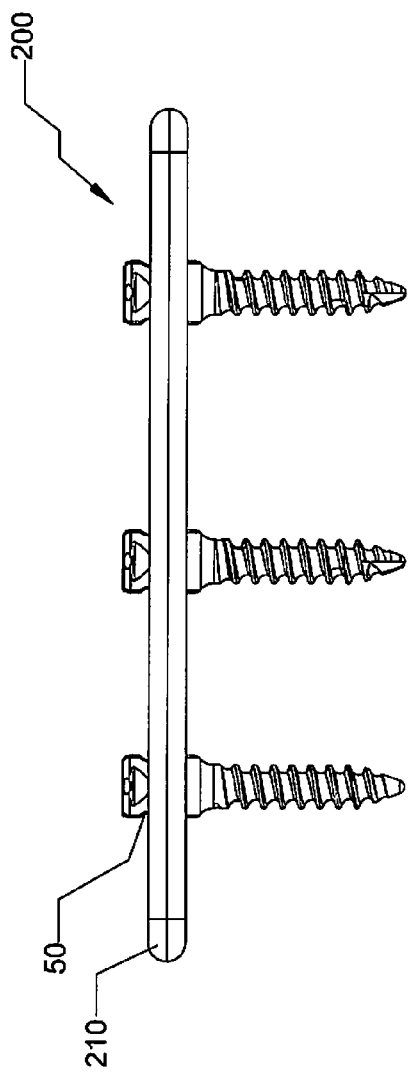
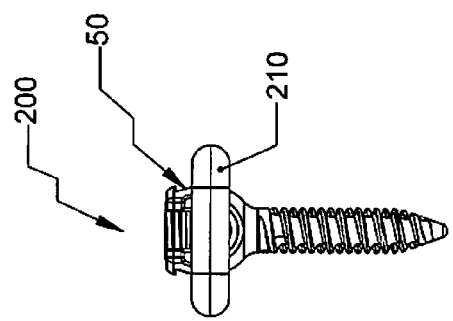
FIG. 5
FIG. 6

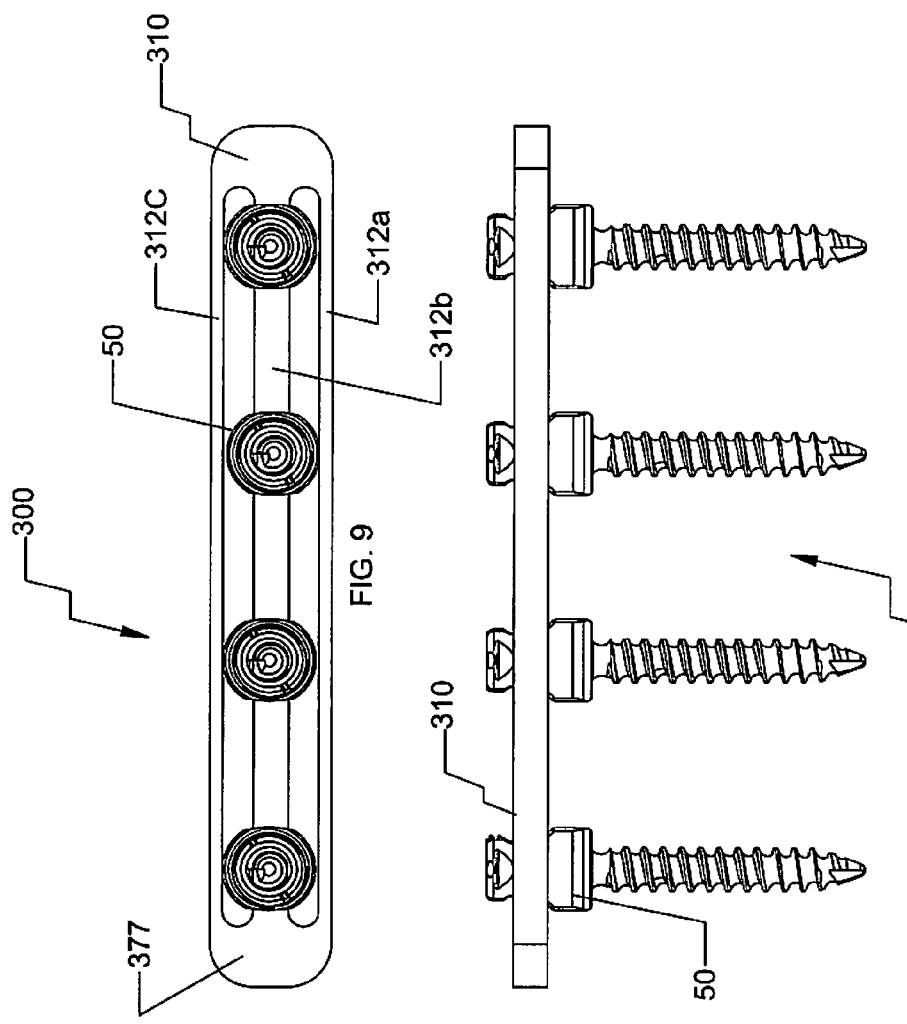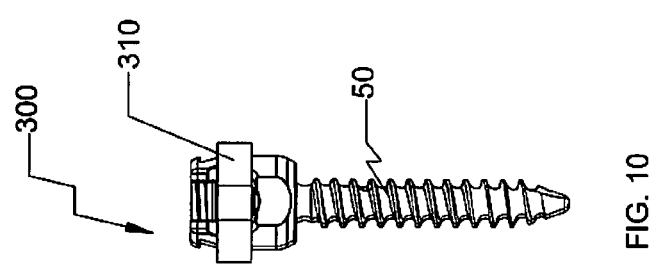

SPINAL STABILIZATION SYSTEM

BACKGROUND

1. Technical Field

The present disclosure relates to orthopedic surgical devices and, more particularly, to a spinal stabilization system.

2. Background of Related Art

The spinal column is a complex system of bones and connective tissues that provide support for the human body and protection for the spinal cord and nerves. The adult spine is comprised of an upper and lower portion. The upper portion contains twenty-four discrete bones, which are subdivided into three areas including seven cervical vertebrae, twelve thoracic vertebrae, and five lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases and types of injury, which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages and cadaver and human bone implants. In order to facilitate stabilizing the spine and keeping the interbody in position, other implants are commonly employed, such as bone screws and rods. Depending on the pathology and treatment, a surgeon will select the appropriate spinal rod material and size, specifically, the cross-sectional diameter.

To meet the problem of providing a rigid pedicle screw and rod construct, especially for addressing the demands of stiff deformity corrections, larger rod constructs have been made to improve the strength of the screw and rod construct. However when large deformity corrections need to be made, these rods are not always strong enough. Larger diameter stainless steel rods have been made for these applications, but a larger rod requires a larger mating screw head to contain the rod, which in turn increases the profile of the construct. In addition, in order to reduce the likelihood of material incompatibility in vivo, the screw assembly also needs to be made of stainless steel to match the rod material, which is not a cost effective alternative.

Therefore, a need exists for a cost effective, rigid screw and rod construct that can still maintain a low profile.

SUMMARY

In accordance with an embodiment of the present disclosure, there is provided a spinal stabilization system including an elongated loop member and a bone screw. The elongated loop member includes a pair of opposing elongate bodies defining a gap therebetween and a pair of connection members connecting the pair of opposing elongate bodies at opposite ends of the elongate bodies. The bone screw includes a head portion defining a slot, a shank extending longitudinally from the head portion, and a set screw. The slot includes a leading end portion configured to receive at least a portion of the elongated loop member and a trailing end portion adapted to receive the set screw. The gap is dimensioned to receive at least a portion of the bone screw securely connected to one of the pair of opposing elongate bodies. The gap is configured and dimensioned to facilitate unilateral adjustment of the elongated loop member relative to the bone screw.

In an embodiment, at least one of the pair of opposing elongate bodies may have a circular-cross section. The leading end portion of the slot may have an arcuate profile to accommodate the circular cross-section of the at least one of the pair of opposing elongate bodies. Additionally, the connection members may have a circular cross-section. Alternatively, at least one of the pair of opposing elongate bodies may have a non-circular cross-section.

In another embodiment, the elongated loop member may be monolithically formed as a unitary construct.

In still yet another embodiment, the width of the gap may be dimensioned to partially receive only a single bone screw securely connected to one of the pair of opposing elongate bodies at a particular longitudinal position.

In accordance with yet another embodiment of the present disclosure, there is provided a spinal stabilization system including an elongated loop member and a bone screw. The elongated loop member includes first, second, and third elongate bodies and a pair of connection members connecting the first, second, and third elongate bodies at opposite ends of the first, second, and third elongate bodies. The first and second elongate bodies define a first gap therebetween and the second, and third elongate bodies define a second gap therebetween. The bone screw includes a head portion defining a slot, a shank extending longitudinally from the head portion and a set screw. The slot includes a leading end portion configured to receive at least a portion of the elongated loop member and a trailing end portion adapted to receive the set screw. The first and second gaps are dimensioned to receive at least a portion of the bone screw securely connected to any one of the first, second, and third elongate bodies. The first and second gaps are configured and dimensioned to facilitate unilateral adjustment of the elongated loop member relative to the bone screw.

In an embodiment, the first, second, and third elongate bodies may have a circular-cross section. Alternatively, the first, second, and third elongate bodies may have a non-circular cross-section. In addition, the first, second, and third elongate bodies may have the same dimensions. In other embodiment, the second elongate body may have a greater diameter than the diameters of the first and second elongate bodies. Moreover, the elongated loop member may define a planar surface configured and dimensioned to engage the set screw.

In another embodiment, the connection portion may include an arcuate configuration. The elongated loop member and the bone screws may be made of the same material. In particular, the elongated loop member may be made of titanium or titanium alloy.

In yet another embodiment, the first, second, and third elongate bodies may be substantially parallel. The width of the first and second gaps may be dimensioned such that only a portion of a single bone screw is received therein. The second elongate body may define a planar surface configured and dimensioned to engage the set screw. In still yet another embodiment, the bone screw may be a taper lock type screw.

BRIEF DESCRIPTION OF THE DRAWINGS

The foregoing and other features of the present disclosure will become apparent to one skilled in the art to which the present disclosure relates upon consideration of the following description of the disclosure with reference to the accompanying drawings, wherein:

FIG. 2 is a side view of the spinal stabilization system of FIG. 1;

FIG. 3 is a front view of the spinal stabilization system of FIG. 1;

FIG. 5 is a side view of the spinal stabilization system of FIG. 4;

FIG. 6 is a front view of the spinal stabilization system of FIG. 4;

FIG. 8 is a side view of the spinal stabilization system of FIG. 7;

FIG. 9 is a top view of the spinal stabilization system of FIG. 7; and

FIG. 10 is a front view of the spinal stabilization system of FIG. 7.

DETAILED DESCRIPTION OF EMBODIMENTS

Figure 1:
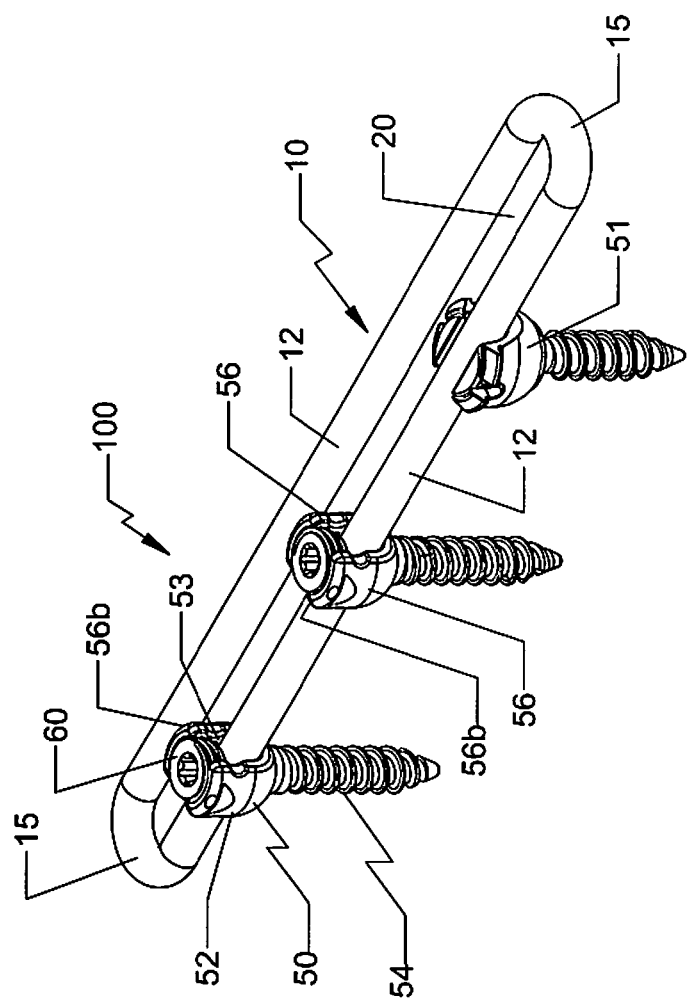
FIG. 1 is a perspective view of a spinal stabilization system in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

With reference to FIGS. 1-3, an embodiment of the present disclosure is shown generally as a spinal stabilization system 100. Spinal stabilization system 100 includes at least one bone screw 50 and an elongated loop member 10. Bone screw 50 includes a head portion 52 configured to receive a portion of elongated loop member 10 therein, a shank 54 extending longitudinally from head portion 52, and a set screw 60 threadably coupled to head portion 52 to secure elongated loop member 10 within head portion 52. Head portion 52 of bone screw 50 includes a pair of radially opposing walls 56 defining a slot 53 therebetween. Radially opposing walls 56 include internal threads (not shown) configured for engaging external threads of set screw 60. Slot 53 defines a U-shaped channel configured and dimensioned to receive elongated loop member 10. Slot 53 includes a leading end portion 53a (FIG. 3) and a trailing end portion 53b (FIG. 3). In particular, leading end portion 53a has an arcuate configuration configured to accommodate the circular cross-section of elongated loop member 10 for a secure fit therein. Trailing end portion 53b of slot 53 defines a substantially planar surface such that when set screw 60 is threadably coupled to head portion 52, a top surface of set screw 60 is substantially flush with trailing end portion 56b of the respective walls 56 of head portion 52 of screw 50.

With continued reference to FIGS. 1-3, shank 54 includes threads 55 to facilitate insertion into vertebral bodies or other bones. Bone screw 50 may be made of a biocompatible material such as Titanium (Ti—CP) and its alloys (e.g., Ti-6Al-4V), Cobalt-Chrome Alloy (CoCr), or Stainless Steel (SS). In particular, head portion 52 and shank 54 may be monolithically formed.

Elongated loop member 10 is configured and dimensioned to be selectively and releasably secured to bone screw 50. Elongated loop member 10 has a closed loop configuration. Elongated loop member 10 includes a pair of opposing elongate bodies 12 of a particular length connected to each other by a pair of opposing connection members 15. The pair of opposing elongate bodies 12 defines a gap 20 therebetween. The width of gap 20 is dimensioned to receive only a portion of a single bone screw 50 such that only a single bone screw 50 can be secured to a particular longitudinal position on either elongate body 12 of the pair of elongate bodies 12. In this manner, gap 20 serves as a guide in unilateral adjustment of elongated loop member 10 relative to bone screws 50. Alternatively, the width of gap 20 may be dimensioned to accommodate bone screws 50 on both elongate bodies 12 at a particular longitudinal position.

Elongated loop member 10 has a uniform cross-section and diameter. Elongate loop member 10 is made of a biocompatible material such as Titanium (Ti—CP) and its alloys (e.g., Ti-6Al-4V), Cobalt-Chrome Alloy (CoCr), or Stainless Steel (SS). The pair of elongate bodies 12 and connection members 15 may be monolithically formed as a unitary construct. For example, elongated loop member 10 may be machined from a single piece of bar stock. In addition, elongate loop member 10 may be surface treated to provide a desired surface roughness to, e.g., facilitate longitudinal movement of elongated loop member 10 when elongated loop member 10 is partially secured with bone screws 50 to enable adjustment of the position of elongated loop member 10. Alternatively, the surface roughness may be chosen to inhibit slippage between elongated loop member 10 and bone screws 50 when elongated loop member 10 is secured with bone screw 50.

Elongate bodies 12 and connection members 15 have a substantially circular cross-section conforming to the contour of the arcuate configuration of leading end portion 53a of slot 53. In this manner, a relative movement between elongated loop member 10 and bone screw 50 in the direction other than the longitudinal direction of elongate body 12 is minimized, which in turn reduces the likelihood of inadvertent loosening or detachment of set screw 60 from head portion 52. Moreover, elongated loop member 10 and bone screw 50 construct affords greater rigidity and strength in comparison with ordinary circular rods having a single elongate member. It is further contemplated that bone screws 50 may be attached to connection member 15, if needed or desired.

While bone screws 50 illustrated in FIGS. 1-3 is a monoaxial set screw type bone screw, it is further contemplated that the plurality of bone screws may be a taper lock screw such as, e.g., a multi-planar taper lock screw, that enables manipulation of a screw shaft about multiple axes, whereby the bone screw is capable of securing elongated loop member 10 with the bone screw on multiple vertebral bodies that are aligned in the spinal column on different planes due to the natural curvature of the spine. However, it is also envisioned that the bone screws may be, e.g., fixed angle screws, uniplanar screws or monoaxial taper lock screws.

A suitable multi-planar taper lock bone screw includes a dual layered housing and a screw shaft having a spherically configured screw head rotatably coupled with housing. In particular, the dual layered housing includes an outer housing and an inner housing. The outer housing can be selectively positioned relative to the inner housing to fully lock the screw head and the connecting rod in position within the inner housing or alternatively to selectively partially lock screw head and/or connecting rod in position while permitting a sliding and/or rotating motion of the connecting rod relative to screw head, and the screw head relative to the bone screw, respectively. Specifically, the outer housing is configured such that at least a portion of an the inner surface of outer housing is capable of sliding over a portion of an outer surface of inner housing in upward and downward directions along the longitudinal axis of bone screw. When outer housing is slid upward in relation to inner housing an inner surface of outer housing causes inner housing to impart compressive force radially inward to secure connecting rod 10 at least partially disposed therein.

One suitable taper lock screw is commercially available from K2M, Inc. (Leesburg, Va.) under the trade name MESA™. In addition, suitable multi-planar taper lock screws are shown and described in U.S. Patent Application Publication 2008/0027432 and in U.S. Patent Application Publication 2007/0093817, both of which are herein incorporated by reference in their entireties. It is contemplated that other types of screws such as, e.g., a fixed screw in which the head of the screw has no movement relative to the screw shaft, a monoaxial screw such as that disclosed in U.S. Patent Application Publication 2009/0105716, and a uni-axial screw such as that disclosed in U.S. Patent Application Publication 2009/0105769 may be utilized. Suitable mono-axial and uni-axial screws are also commercially available under the trade name MESA™.

It is also envisioned that spinal stabilization system 100 may be used with other surgical instruments such as, e.g., a rod reduction device, configured to reduce a rod into position in a rod receiving slot in a head of a bone screw with a controlled, measured action. Reference may be made to U.S. Patent Application Publication Nos. 2009-0018593 and 2011-0087298, the entire contents of each of which are incorporated herein by reference, for a detailed discussion of the construction and operation of a rod reduction device.

In use, the user implants a plurality of bone screws 50 in vertebral bodies of a patient. Threaded shank 54 can be driven into the desired vertebral body by providing torsional force via a driving tool (not shown) configured to mate with and grip bone screw 50. After shank 54 is positioned within the vertebral body and the driving tool is removed from bone screw 50, elongated loop member 10 is positioned within the respective slots 53 of bone screws 50. At this time, the surgeon can position set screws 60 in respective head portions 20 of bone screws 50 and partially lock set screws 60 in the respective head portions 20 to enable unilateral adjustment of elongated loop member 10 relative to bone screw 50. Upon determining a desired location of elongated loop member 10, the surgeon can further tighten set screws 60 to securely fix elongated loop member 10 with bone screws 50.

The rod and bone screw combination of the present disclosure may provide particular advantages in, e.g., scoliosis, or other spinal deformity surgery in which high stress levels are exerted upon such constructs at particular levels in the construct or over the entire length of such a construct.

Figure 4:
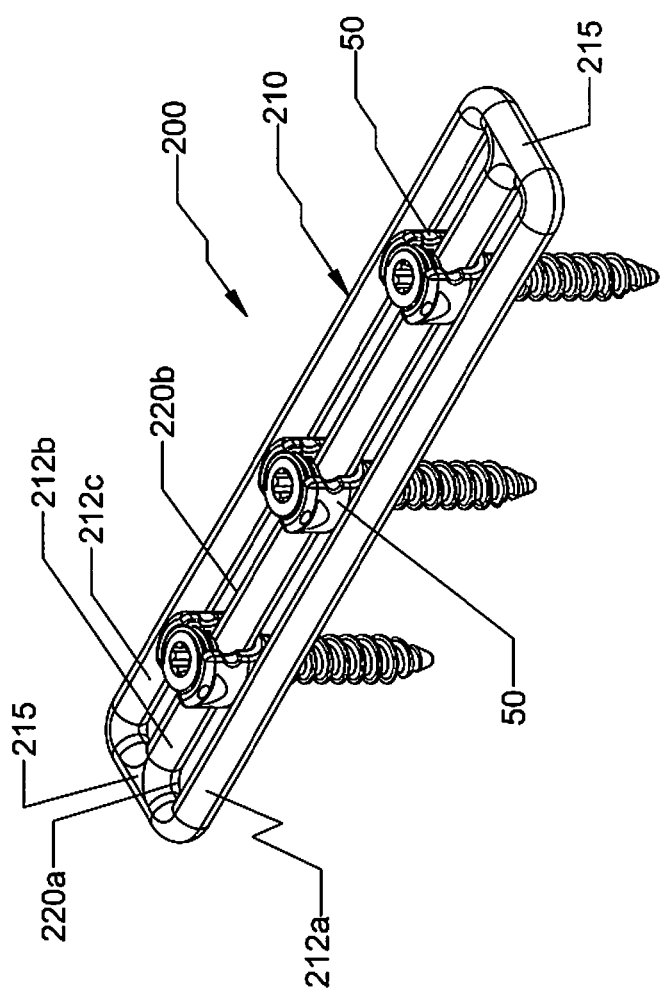
FIG. 4 is a perspective view of a spinal stabilization system in accordance with another embodiment of the present disclosure.
Figure 7:
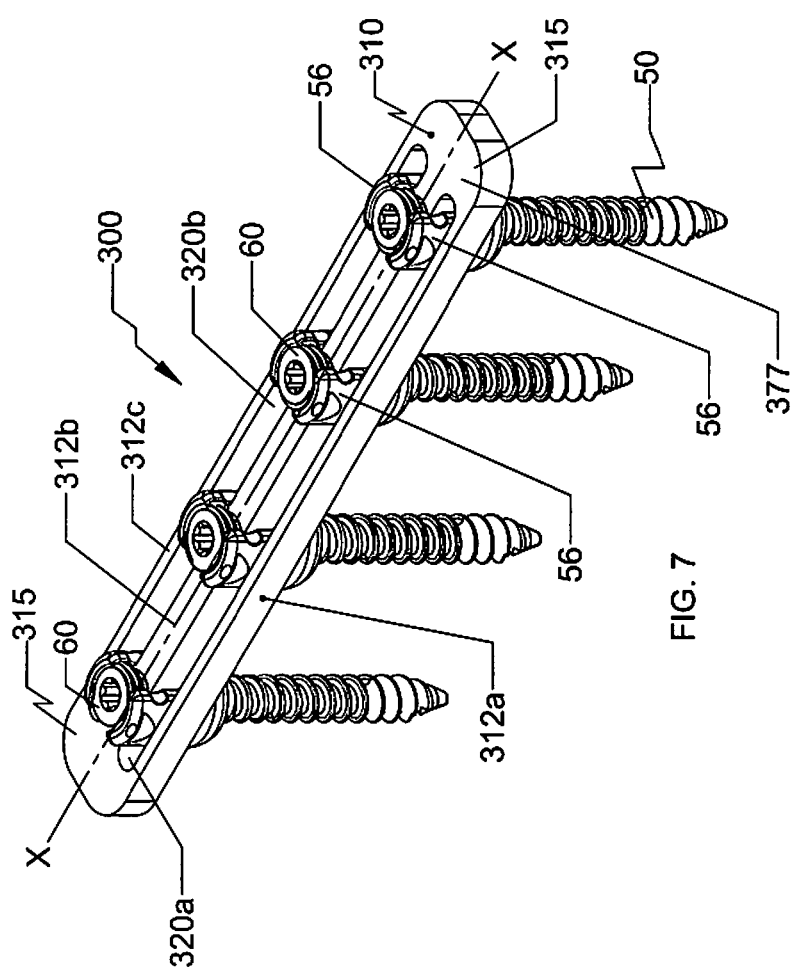
FIG. 7 is a spinal stabilization system in accordance with yet another embodiment of the present disclosure.

With reference now to FIGS. 4-6, a spinal stabilization system in accordance with another embodiment of the present disclosure is shown generally as 200. Spinal stabilization system 200 includes at least one bone screw 50 and an elongated loop member 210. Bone screw 50 is identical to bone screw 50 described hereinabove and will not be described.

Elongated loop member 210 is configured and dimensioned to be selectively and releasably secured to bone screws 50. Elongated loop member 210 has double loop configuration. In particular, elongated loop member 210 includes first, second, and third elongate bodies 212a, 212b, 212c. First, second, and third elongate bodies 212a, 212b, 212c of a particular length are connected to each other by a pair of opposing connection members 215. First and second elongate bodies 212a, 212b define a first gap 220a therebetween. Second and third elongate bodies 212b, 212c define a second gap 220b therebetween. The width of gaps 220a, 220b may be dimensioned such that only a single bone screw 50 may be secured to a particular longitudinal position on elongated loop member 210. Alternatively, the width of gap 220a, 220b may be dimensioned to accommodate bone screws 50 on first, second, and third elongate bodies 212a, 212b, 212c at the same longitudinal position.

Elongated loop member 210 has a uniform cross-section and diameter. Elongate loop member 210 is made of a biocompatible material such as Titanium (Ti—CP) and its alloys (e.g., Ti-6Al-4V), Cobalt-Chrome Alloy (CoCr), or Stainless Steel (SS). Elongate bodies 212a, 212b, 212c and connection members 215 may be monolithically formed as a unitary construct.

Elongate bodies 212a, 212b, 212c and connection members 215 have a substantially circular cross-section conforming to the contour of the arcuate configuration of leading end portion 53a of slot 53 (FIG. 3). In this manner, a relative movement between elongated loop member 210 and bone screw 50 in the direction other than the longitudinal direction of elongated loop member 210 is minimized, which in turn reduces the likelihood of inadvertent loosening or detachment of set screw 60 from head portion 52. Moreover, by having a double loop configuration, bone screw 50 may be secured with elongate body 212b to provide symmetric flexural rigidity of elongated loop member 210 by having elongate bodies 212a, 212c on respective lateral sides of elongate body 212b. In addition, elongated loop member 210 offers an additional elongate body 212c, which enables surgeon to secure elongated loop member 210 to additional bone screws 50, as needed or desired, based on the surgical procedure being performed.

While bone screws 50 illustrated in FIGS. 4-6 are monoaxial set screw type bone screws, it is further contemplated that the plurality of bone screws may be a taper lock screw such as, e.g., a multi-planar taper lock screw, that enables manipulation of a screw shaft about multiple axes, whereby the bone screw is capable of securing elongated loop member 210 with the bone screw on multiple vertebral bodies that are aligned in the spinal column on different planes due to the natural curvature of the spine. However, it is also envisioned that the bone screws may be, for example, fixed angle screw, uniplanar screws, monoaxial taper lock screws, or combinations of these screws.

Spinal stabilization system 200 may be used in a manner substantially identical to that of spinal stabilization system 100, and thus, will not be described herein.

With reference now to FIGS. 7-10, a spinal stabilization system in accordance with yet another embodiment of the present disclosure is shown generally as 300. Spinal stabilization system 300 includes a plurality of bone screws 50 (described hereinabove) and an elongated loop member 310. Elongated loop member 310 is configured and dimensioned to be selectively and releasably secured to bone screws 50. Elongated loop member 310 has double loop configuration. In particular, elongated loop member 310 includes first, second, and third elongate bodies 312a, 312b, 312c. First, second, and third elongate bodies 312a, 312b, 312c of a particular length are connected to each other by a pair of opposing connection members 315. First and second elongate bodies 312a, 312b define a first gap 320a therebetween. Second and third elongate bodies 312b, 312c define a second gap 320b therebetween. Second elongate body 312b is configured to be secured with bone screw 50. Gaps 320a, 320b and first and third elongate bodies 312a, 312c guide bone screws 50 during unilateral adjustment of elongated loop member 310. In particular, gaps 320a, 320b are dimensioned such that only a single bone screw 50 may be secured to a particular longitudinal position on elongated loop member 310. Under such a configuration, any lateral movement between elongated loop member 310 and bone screws 50 is minimized. Such a configuration facilitates unilateral adjustment of elongated loop member 310 along a longitudinal axis "X-X."

With particular reference to FIG. 9, elongate body 312b has square shaped cross-section. In particular, elongate body 312b has a reinforced thickness to accommodate securement of bone screws 50 thereon. In addition, elongated loop member 310 defines at least one planar surface 377. Under such a configuration, a set screw 60 may have a greater surface contact with elongate body 312b, which may reduce slippage and minimize inadvertent loosening and detachment of set screw 60. Elongate loop member 310 is made of a biocompatible material such as Titanium (Ti—CP) and its alloys (e.g., Ti-6Al-4V), Cobalt-Chrome Alloy (CoCr), or Stainless Steel (SS). Elongate bodies 312a, 312b, 312c and connection members 315 are monolithically formed as a unitary construct.

While bone screws 50 used with elongated loop member 310 are monoaxial set screw type bone screw, it is further contemplated that the plurality of bone screws may be a taper lock screw such as, e.g., a multi-planar taper lock screw, that enables manipulation of a screw shaft about multiple axes, whereby the bone screw is capable of securing elongated loop member 310 with the bone screw on multiple vertebral bodies that are aligned in the spinal column on different planes due to the natural curvature of the spine. However, it is also envisioned that the bone screws may be, for example, fixed angle screw, uniplanar screws or monoaxial taper lock screws.

Spinal stabilization system 300 may be used in a manner substantially identical to that of spinal stabilization system 100, and thus, will not be described herein.

Elongated loop member 310 provides a greater stiffness and rigidity than circular rods having comparable dimensions in various materials. As such, elongated loop member 310 and bone screw 50 construct affords greater rigidity and strength. In addition, such construct, as shown, does not require any design changes to taper lock screw 50, and thus advantageously provides efficiency of manufacture and inventory.

Although the illustrative embodiments of the present disclosure have been described herein with reference to the accompanying drawings, the above description, disclosure, and figures should not be construed as limiting, but merely as exemplifications of particular embodiments. For example, it is contemplated that the cross-section of elongate bodies 312a, 312b, 312c need not be square. Rather, elongate bodies 312a, 312b, 312c may be rectangular, elliptical or any other cross-section to add rigidity to elongated loop member 310. In addition, a taper lock screw 51 (FIG. 1) may be used with any embodiment of spinal stabilization system 100, 200, 300. One skilled in the art will recognize that the present disclosure is not limited to use in spine surgery, and that the instrument and methods can be adapted for use with any suitable surgical device. It is to be understood, therefore, that the disclosure is not limited to those precise embodiments, and that various other changes and modifications may be effected therein by one skilled in the art without departing from the scope or spirit of the disclosure.

What is claimed is:

1. A spinal stabilization system comprising:
   an elongated loop member including a pair of opposing elongate bodies defining a gap therebetween and a pair of connection members connecting the pair of opposing elongate bodies at opposite ends of the elongate bodies, at least one elongate body having a square shaped cross-section; and
   a bone screw including a head portion defining a slot, a shank extending longitudinally from the head portion, and a set screw, the slot including a leading end portion configured to receive at least a portion of the elongated loop member and a trailing end portion adapted to receive the set screw, wherein the gap is dimensioned to receive at least a portion of the bone screw securely connected to one of the pair of opposing elongate bodies, the gap configured and dimensioned to facilitate unilateral adjustment of the elongated loop member relative to the bone screw, wherein the square shaped cross-section of the at least one elongate body is dimensioned for non-rotatable movement of the head portion of the bone screw along the at least one elongate body.

2. The spinal stabilization system according to claim 1, wherein the elongated loop member is monolithically formed as a unitary construct.

3. The spinal stabilization system according to claim 1, wherein a width of the gap is dimensioned to partially receive only a single bone screw securely connected to one of the pair of opposing elongate bodies at a particular longitudinal position.

4. A spinal stabilization system comprising:
   an elongated loop member including first, second, and third elongate bodies and a pair of connection members connecting the first, second, and third elongate bodies at opposite ends of the first, second, and third elongate bodies, the first and second elongate bodies defining a first gap therebetween, the second and third elongate bodies defining a second gap therebetween; and
   a bone screw including a head portion defining a slot, a shank extending longitudinally from the head portion, and a set screw, the slot including a leading end portion configured to receive at least a portion of the elongated loop member and a trailing end portion adapted to receive the set screw, wherein the first and second gaps are dimensioned to receive at least a portion of the bone screw securely connected to any one of the first, second, and third elongate bodies, the first and second gaps configured and dimensioned to facilitate unilateral adjustment of the elongated loop member relative to the bone screw, wherein at least one of the first, second, or third elongate bodies has a square shaped cross-section configured for non-rotatable movement of the head portion of the bone screw along the at least one of the first, second, or third elongate bodies.

5. The spinal stabilization system according to claim 4, wherein the first, second, and third elongate bodies have the same dimensions.

6. The spinal stabilization system according to claim 4, wherein the second elongate body has a greater width than widths of the first and second elongate bodies.

7. The spinal stabilization system according to claim 4, wherein the elongated loop member defines a planar surface configured and dimensioned to engage the set screw.

8. The spinal stabilization system according to claim 4, further including a taper lock type screw.

9. The spinal stabilization system according to claim 4, wherein the connection portion includes an arcuate configuration.

10. The spinal stabilization system according to claim 4, wherein the elongated loop member and the bone screws are made of the same material.

11. The spinal stabilization system according to claim 10, wherein the elongated loop member is made of titanium or titanium alloy.

12. The spinal stabilization system according to claim 4, wherein the first, second, and third elongate bodies are substantially parallel.

13. The spinal stabilization system according to claim 4, wherein widths of the first and second gaps are dimensioned such that only a portion of a single bone screw is received therein.

14. The spinal stabilization system according to claim 4, wherein the second elongate body defines a planar surface configured and dimensioned to engage the set screw.

\* \* \* \* \*